United States Patent
Fraden

(10) Patent No.: US 9,504,385 B2
(45) Date of Patent: Nov. 29, 2016

(54) MEDICAL PROBE WITH CONSISTENT ACTION

(75) Inventor: Jacob Fraden, San Diego, CA (US)

(73) Assignee: KAZ, Inc., Southborough, MA (US)

( * ) Notice: Subject to any disclaimer, the term of this patent is extended or adjusted under 35 U.S.C. 154(b) by 1778 days.

(21) Appl. No.: 12/557,156

(22) Filed: Sep. 10, 2009

(65) Prior Publication Data

US 2010/0030099 A1 Feb. 4, 2010

Related U.S. Application Data

(63) Continuation of application No. 11/529,000, filed on Sep. 29, 2006.

(60) Provisional application No. 60/727,938, filed on Oct. 19, 2005.

(51) Int. Cl.
- A61B 5/00 (2006.01)
- A61B 5/103 (2006.01)
- A61B 5/117 (2016.01)
- A61B 5/01 (2006.01)

(52) U.S. Cl.
CPC .............. *A61B 5/00* (2013.01); *A61B 5/6843* (2013.01); *A61B 5/01* (2013.01)

(58) Field of Classification Search
CPC ...................................................... A61B 5/00
USPC .............. 600/587, 548, 549, 490, 500, 595; 607/75, 145, 151, 116; 604/198
See application file for complete search history.

(56) References Cited

U.S. PATENT DOCUMENTS

| | | | |
|---|---|---|---|
| 4,209,021 A | | 6/1980 | Warming |
| 4,295,467 A | * | 10/1981 | Mann et al. ............. 606/44 |
| 4,860,753 A | * | 8/1989 | Amerena ............. 600/306 |
| 4,863,281 A | * | 9/1989 | Suszynski ............. 374/158 |
| 4,993,424 A | * | 2/1991 | Suszynski et al. ......... 600/549 |
| 5,012,816 A | | 5/1991 | Lederer |
| 5,317,125 A | * | 5/1994 | Rossi ............. B23K 11/252 219/110 |
| 5,818,246 A | | 10/1998 | Zhong |
| 7,338,206 B2 | * | 3/2008 | Yu ............. 374/208 |
| 7,651,265 B2 | * | 1/2010 | Yang et al. ............. 374/121 |
| D637,922 S | * | 5/2011 | Puglisi et al. ............. D10/60 |
| 2004/0047392 A1 | * | 3/2004 | Wu et al. ............. 374/121 |
| 2004/0095985 A1 | * | 5/2004 | Ko et al. ............. 374/100 |
| 2004/0176754 A1 | * | 9/2004 | Island et al. ............. 606/9 |
| 2004/0243021 A1 | | 12/2004 | Murphy et al. |
| 2005/0003518 A1 | * | 1/2005 | Aviram et al. ............. 435/287.1 |
| 2005/0043631 A1 | | 2/2005 | Fraden |
| 2005/0131342 A1 | * | 6/2005 | Haar et al. ............. 604/68 |
| 2006/0120432 A1 | | 6/2006 | Lantz et al. |
| 2008/0132842 A1 | * | 6/2008 | Flaherty ............. 604/151 |
| 2008/0285618 A1 | * | 11/2008 | Chen ............. 374/121 |

* cited by examiner

*Primary Examiner* — Rene Towa
*Assistant Examiner* — May Abouelela
(74) *Attorney, Agent, or Firm* — Wood Herron & Evans LLP

(57) ABSTRACT

A probe for intermittent contacting a patient body with a predetermined speed and force. Initially, the probe is recessed inside the device which is brought in contact with the patient body, while keeping the probe from making a contact with the patient. On a command from an operator or control circuit, the probe is deployed moving toward the patient body surface with a substantially consistent force and rate of motion, thus making a contact in a consistent fashion.

19 Claims, 5 Drawing Sheets

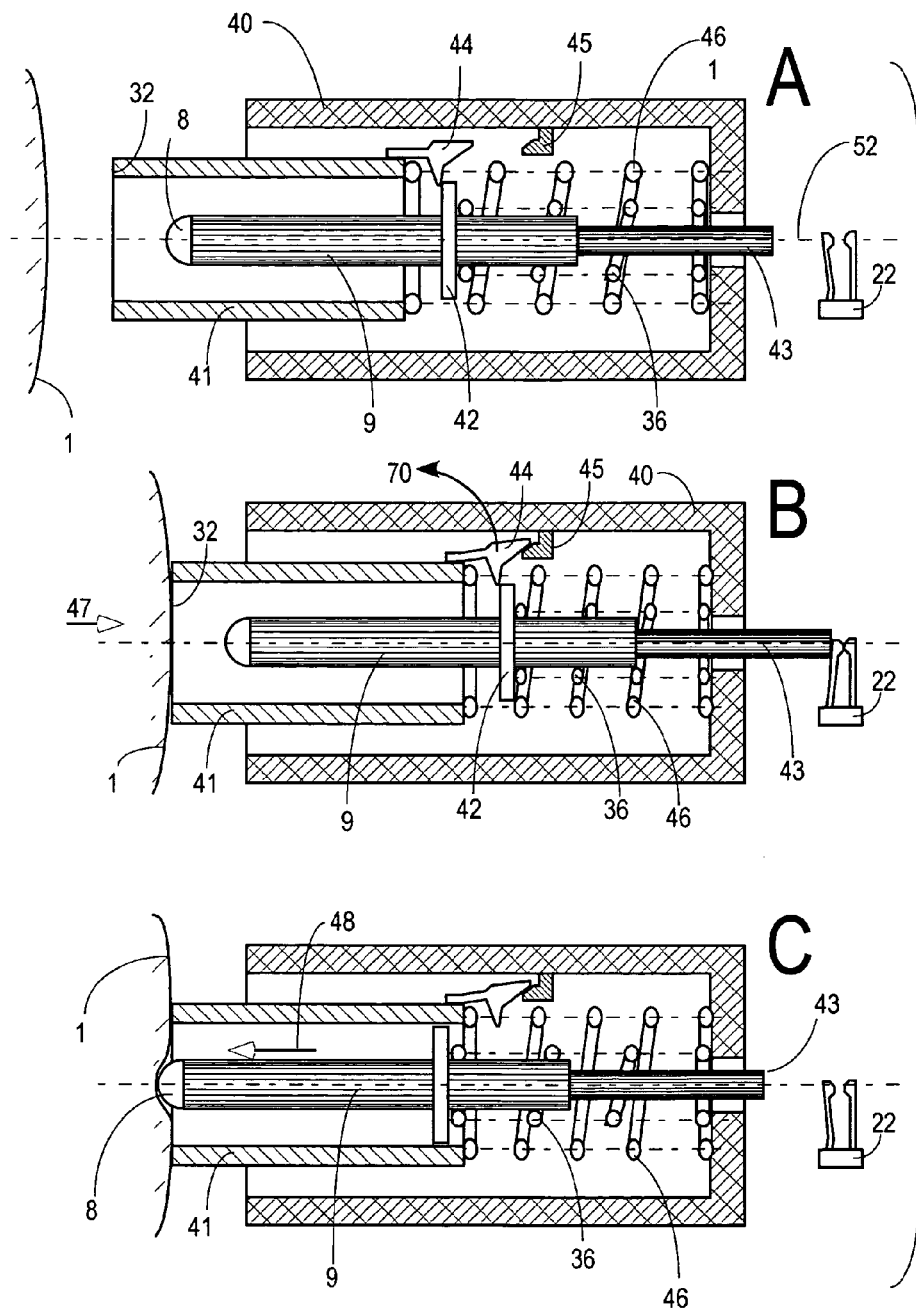

_US 9,504,385 B2_

MEDICAL PROBE WITH CONSISTENT ACTION

CROSS-REFERENCE TO RELATED APPLICATIONS

This application is a continuation of U.S. patent application Ser. No. 11/529,000 (pending) filed on Sep. 29, 2006, which claims the benefit of priority of U.S. Provisional Patent Application Ser. No. 60/727,938 filed Oct. 19, 2005, the disclosures of which are incorporated by reference herein in their entirety.

TECHNICAL FIELD

This invention relates to medical probes. More particularly it relates to probes of the intermittent thermometers for detecting temperature from the surface of a patient.

BACKGROUND

Medical information may be obtained either from the interior of a body or non-invasively from its exterior. Apart from non-contact devices, a sensing probe is being brought in a physical contact with the biological tissue. Such a probe may incorporate some kind of a sensor. Examples of the sensors include a microphone, measuring gauge, light emitters and detectors and a temperature transducer. In some applications, the probe is attached to the patient body on a continuous basis, while in other applications the probe shall be brought intermittently into a contact with the biological tissue (skin, e.g.) to perform some kind of medical procedure, such as measurement or treatment. It may be important for various reasons (accuracy, consistency, rate of the sensor's response, etc.) to bring the probe in contact with the patient body in a consistent manner that is substantially independent of the operator training and operation, patient behavior and other uncontrollable or unpredictable factors. In other words, the probe shall move toward the patient body with a relatively pre-defined speed and come in a contact with a predictable force. One example that is given here by way of a reference is a medical probe with an electromagnetic control taught by Warming in the U.S. Pat. No. 4,209,021. An example of a need to produce a consistent pressure by a probe is a body surface temperature probe of the U.S. Patent Application Publication No. US-2005-0043631-A1. This probe may produce too much of a variability if it is pressed to the skin with a random force thus making an inconsistent thermal contact and modulating the subcutaneous blood perfusion. These factors, in turn, may affect the measured skin temperature. Controlling a rate of the probe deployment toward the skin and the force of a contact is important for such a device.

It is therefore an object of the present invention to provide a means for making a fast and consistent contact between a medical probe and the patient tissue.

Another goal of this invention is to find a way of the probe to be deployed at the moment of forming of a contact between the skin and the medical device.

And another goal of this invention is to develop a method of an intermittent and consistent interaction between the medical probe and the body surface.

SUMMARY

To make a consistent contact between the probe and surface of a patient body, initially, the sensing probe is recessed inside the device which is brought in contact with the patient body, while keeping the probe from making a contact with the patient. On a command from an operator or internal controller, the probe is deployed and moves toward the patient body surface with a substantially constant force and rate of motion, thus making a contact in a consistent fashion.

BRIEF DESCRIPTION OF DRAWINGS

FIG. 10 depicts a cross-sectional view of the third embodiment of the sensor in three positions: A-standby, B-trigger, and C-deployed.

DETAILED DESCRIPTION

Figure 1:
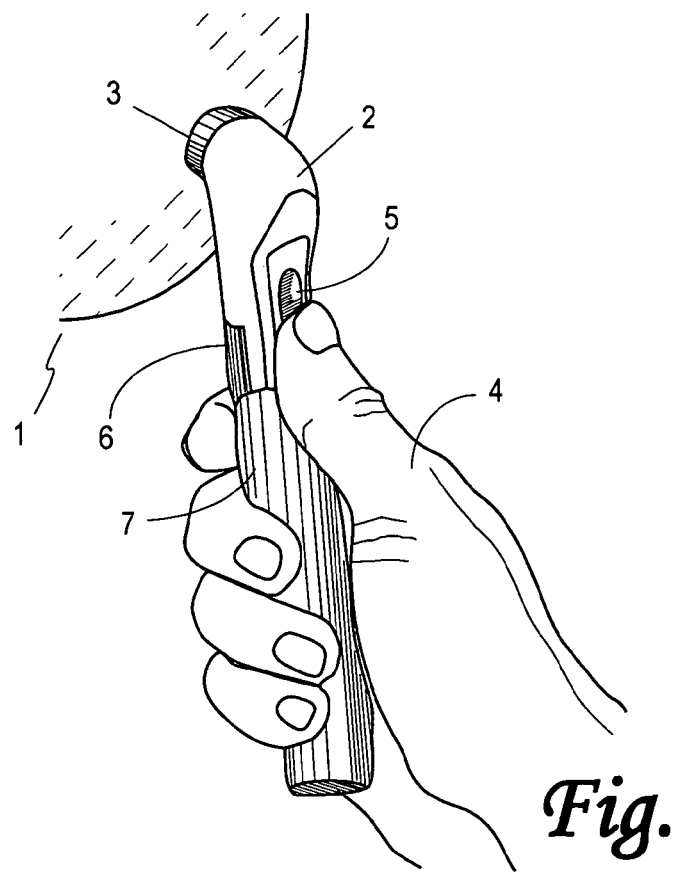
FIG. 1 is a perspective view of a medical device pressing against the patient body.

FIG. 1 illustrates a handheld medical device 7 intended for touching a selected location on skin 1 of a patient's body. Device 7 may incorporate display 6 and control pushbutton 5. The head 3 is brought in a direct contact with the patient. Pushbutton 5 may be actuated by thumb 4. The device may be useful either for taking a measurement, for example, measuring temperature, or for treatment, for example, delivering a medication. In either application, the probe hidden inside the head 3 shall move to the skin 1 with a predetermined speed and force.

Figure 2:
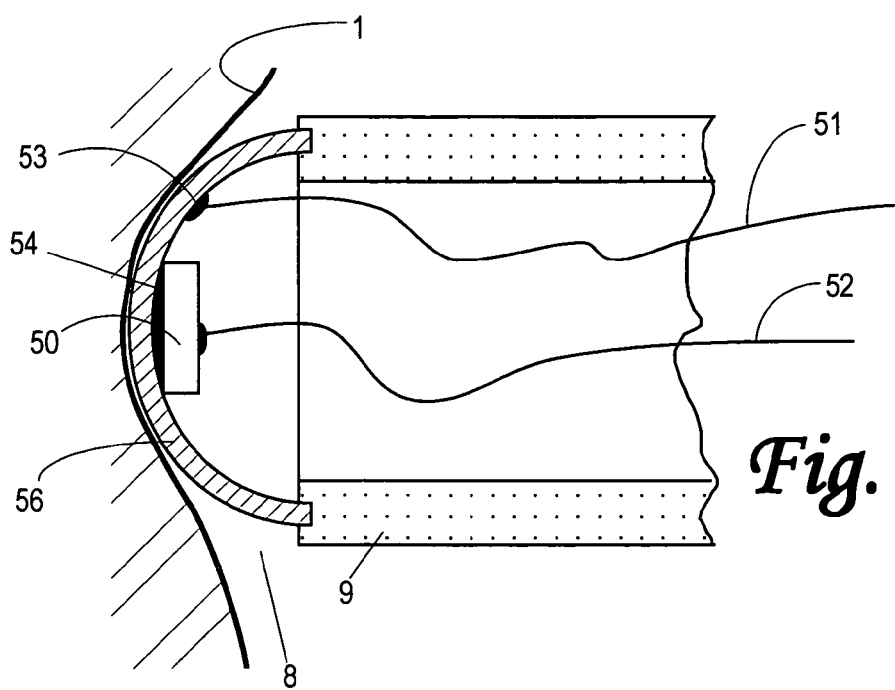
FIG. 2 illustrates a cross-sectional view of a temperature probe.
Figure 3:
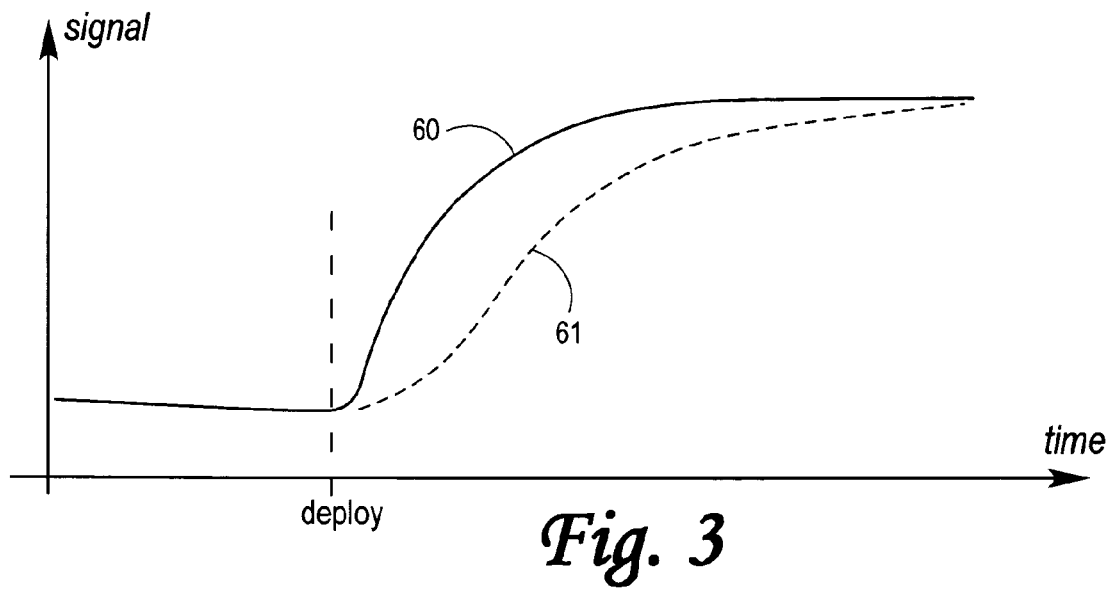
FIG. 3 illustrates variable rates of a response of a temperature sensor.

An example of a contact temperature probe is shown in FIG. 2. Probe 9 is formed as a tube with a hollow interior. Its sensor 8 consists of a flat or dome shaped metal plate 56 where temperature transducer 50 (for example, a thermistor with the top-bottom terminations) is attached by solder or conductive epoxy 54. Connecting wires 51 and 52 make electrical connections between an electronic circuit (not shown) to the transducer 50 and plate 56 at the point 53. After the sensor 8 of the probe 9 is brought in contacts with the patient, plate 56 touches the skin 1 and transfers heat from the skin to transducer 50. The rate of a heat transfer will depend on depth of the impression of plate 56 into the skin 1. As shown in FIG. 3, the shape of the transducer's 50 response may change depending on the force exerted by the sensor 8 and depth of impression (curve 61 represents a result from a shallower impression than curve 60) and in a case when the signal processing relies on that shape, accuracy may be compromised. A cause for such inconsistency may be, for example, a different pressure exerted by a hand of an operator on device 7 when it is brought in coupling with the patient (FIG. 1). To minimize the variability, this invention teaches a way to deploy probe 9 toward the skin in a consistent manner that is substantially independent on the operator's technique.

Figure 4:
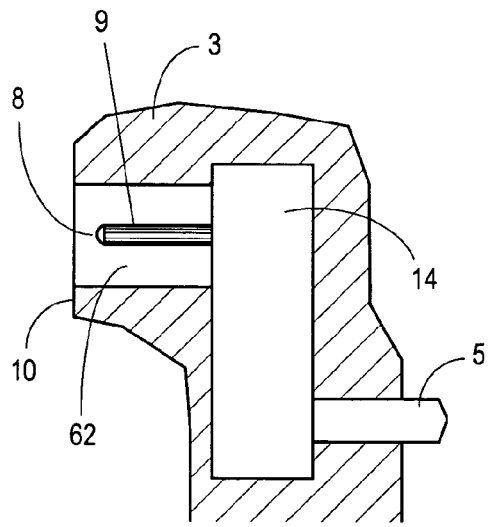
FIG. 4 is a cross-sectional view of the probe of FIG. 1 in a standby mode.
Figure 5:
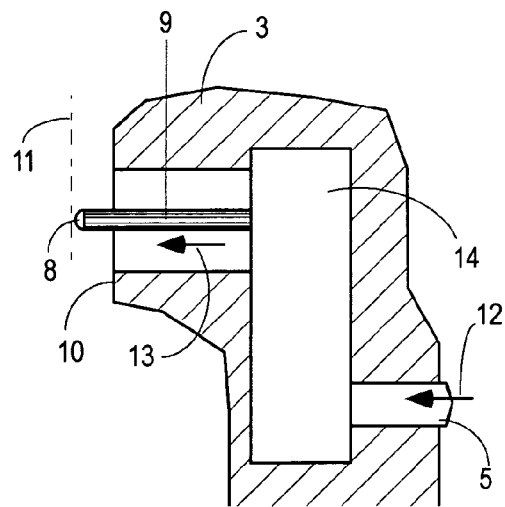
FIG. 5 shows the probe of FIG. 4 with a fully deployed sensor.

FIG. 4 illustrates the sensing head 3 and its interior in a standby state. Probe 9 is recessed inside a cavity 62 of the sensing head 3. Sensor 8 may incorporate a temperature transducer or any other suitable device for measuring or treating a patient. Sensor 8 is positioned at a distal end of probe 9. The outer rim 10 of sensing head 3 may be brought in contact with the patient skin. The rim 10 and the sensing head 3 form a guard around the probe 9. When the rim 10 initially touches the skin, sensor 8 is still not making a contact because it is hidden in a cavity 62 inside the sensing head 3. Probe 9 is attached to a mechanism 14 which, in turn, may be actuated by an electronic circuit (not shown) or alternatively mechanically by depressing pushbutton 5 or by way of pressing rim 10 to the patient skin 1. Now turning to FIG. 5, notice that pushbutton 5 is depressed in direction 12. This initiates operation of the mechanism 14. The mechanism is built and programmed to respond to the pushbutton 5. Upon the pushbutton 5 is pressed, mechanism 14 quickly (within 100 ms or less, e.g.) deploys the probe 9 which moves in direction 13 potentially all the way up to its end position 11. If rim 10 touches the patient skin, sensor 8 will not reach its end position 11 but instead will be pressed against the skin with a specific force, defined by mechanism 14, and stopped.

Figure 6:
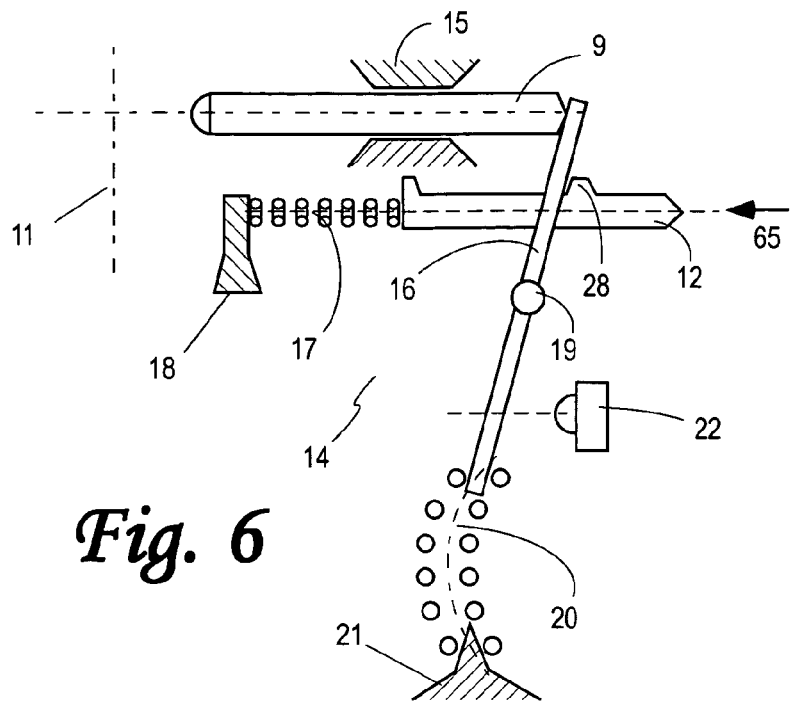
FIG. 6 is a schematic of the first embodiment in a standby mode.

There are several ways of designing the mechanism 14. One example would be use of a solenoid whose core is coupled to probe 9. Other embodiments may include both the electrical and mechanical devices operating with linear and/or rotating motions. The first example of a mechanical embodiment with a manual actuation (FIG. 6) illustrates a mechanism that deploys probe 9 toward the end position 11. The figure shows the mechanism in a "cocked" or stand-by state. Functionality of the mechanism relies on spring 20 that when compressed and tilted, can remain in one of two stable positions where the first position is shown in FIG. 6. The spring 20 is coupled to both the probe 9 and button 12 via a lever 16 which may rotate around pivot 19. Button 12 is forced to the shown position by a return spring 17. The probe 9 is attached to the lever 16 and may move within the guide channel 15. The switch 22 is located in the proximity of lever 16.

Figure 7:
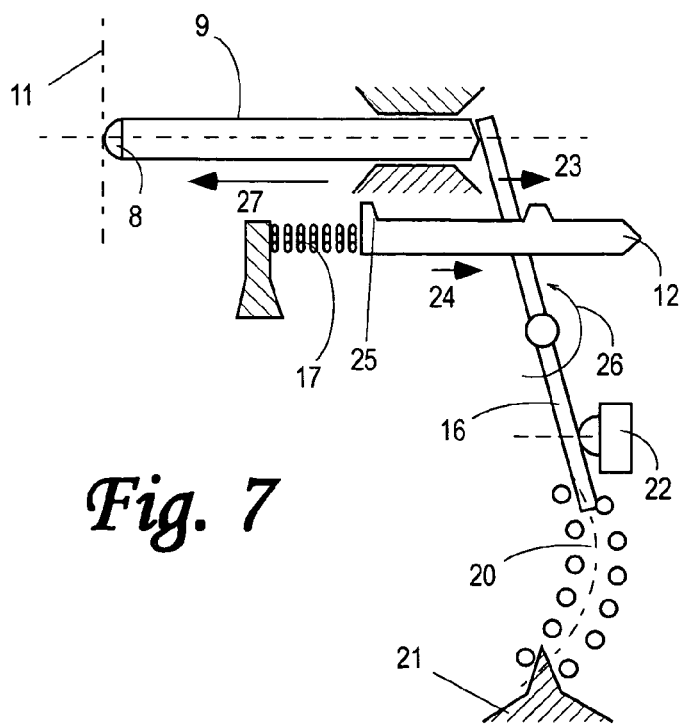
FIG. 7 is the schematic of FIG. 6 with a deployed sensor.

To deploy the probe 9, button 12 is moved in direction indicated by arrow 65. A bump 28 which is part of the button 12 engages with the lever 16 and moves it and subsequently the probe 9 leftward. This causes the spring 20 to compress and tilt toward its unstable position around the support 21. When the spring passes through the unstable position, it quickly snaps toward the second stable position shown in FIG. 7. This snap causes a fast rotation of the lever 16 in a direction indicated by the arrow 26 and the probe 9 quickly moves in a direction 27 toward the end position 11. A rotation of the lever 16 actuates an optional switch 22 that signals the electronic circuit of the probe deployment. As a rule, the sensor 8 will not reach the end position 11 as it will be stopped by the skin surface (not shown) that will be pressed with a predetermined force defined by the properties of spring 20.

To return the mechanism back to its stand-by position of FIG. 6, the button 12 is released. This allows the return spring 17 to move button 12 in a direction 24 and, subsequently slide probe 9 back and snap spring 20 across its unstable position to the first stable position. This re-cocks the mechanism and makes it ready for the next actuation.

Figure 8:
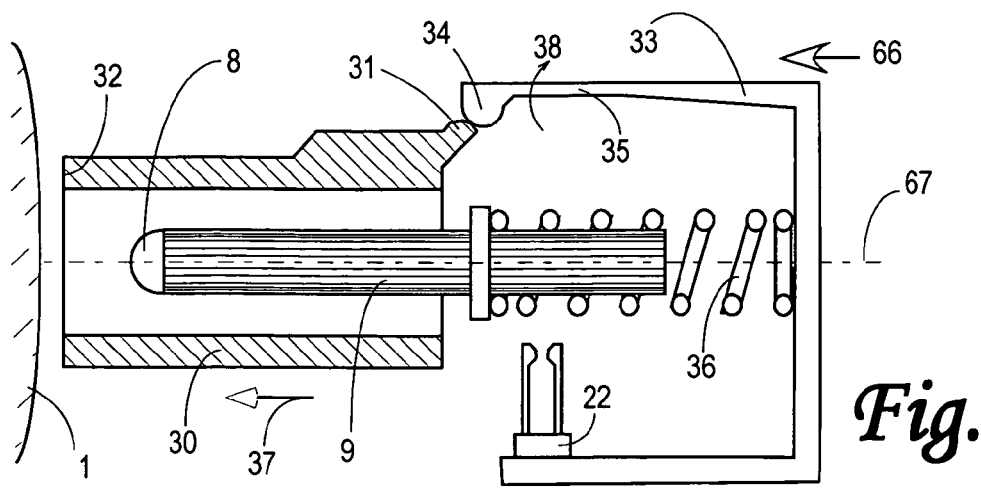
FIG. 8 is a schematic of a second embodiment in a stand-by mode.

The second embodiment of the probe deploying of the medical device mechanism is shown in FIG. 8. It achieves the same result as above by a different method. Instead of releasing the probe toward the patient body, it uses a moving guard 30 that surrounds and encloses the probe 9 in a standby state. When actuated, the guard 30 is allowed to slide by a snap inside the frame 33 (which is a part of the device housing) and allow the probe 9 to protrude outside of the outer rim 32 of the guard so that the sensor 8 will press against the skin 1. The mechanism has the following key components shown in FIG. 8 in a standby state: the probe 9 with the attached sensor 8, the spring 36, guard 30, frame 33 with a finger 34 and optional switch 22. The guard 30 can move back and forth along axis 67. Initially, the guard 30 is locked in a standby position by the tooth 31 that is pressed to the release finger 34. Note that the finger 34 is supported by a resilient neck 35 supported by the frame 33. In this example, switch 22 is normally open.

Figure 9:
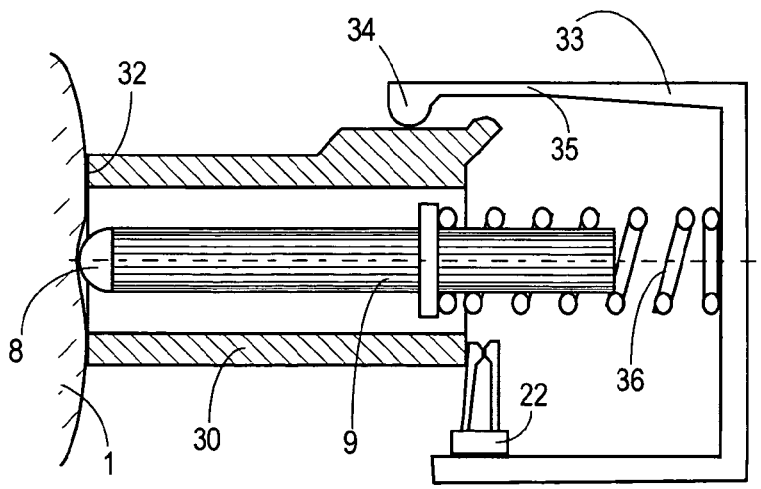
FIG. 9 is the schematic of FIG. 8 with a deployed sensor.

To operate, the outer rim 32 of the guard 30 is pressed against patient body 1 by exerting force onto the frame 33 in a direction 66. This force presses tooth 31 against finger 34 resulting is development of stress in the neck 35. So far, the probe 9 is hidden inside the guard 30 and its sensor 8 is not in contact with patient body 1. When force along direction 66 reaches a specific threshold value, the neck 35 snaps upwardly in direction 38 resulting in decoupling between the finger 34 and tooth 31. The overwhelming force exerted onto the frame 33 of the device moves the entire device (the frame and housing with all internal components) to the left as shown in FIG. 9. Since the finger 34 no longer restricts movement of the guard 30, the latter slides to rightward with respect to probe 9 and frame 33. This allows sensor 8 to move beyond the outer rim 32 and come in a physical contact with patient skin 1. At that moment the guard 30 actuates switch 22 sensing a signal to the internal electronic circuit (not shown) manifesting the device actuation. When the sensor 8 presses against skin 1, the spring 36 compresses, thus exerting a constant force on probe 9. Hence, a sudden and fast engagement of sensor 8 with a patient skin 1 creates a consistent and predictable action that is generally independent on the operator's technique. When the device is removed from the patient body, the mechanism must be re-cocked by sliding guard 30 leftward with respect to the frame 33. This can be done by an additional spring (not shown) or manually.

A third embodiment of the medical device mechanism 14 that illustrates how the probe deployment can be initiated by a contact between the patient and the probe is illustrated in FIG. 10 which shows three stages of the mechanism action. The first Stage A is the mechanism in a standby position. The medical device's housing 40 supports a moving guard 41, the probe 9, two springs 36 and 46, the trigger 44 and pusher 45. The probe 9 comprises a flange 42, shaft 43 and may incorporate at its outer end the sensor 8. A switch 22 is in a normally open state. Both the guard 41 and probe 9 can move along the axis 52 with respect to the housing 40 and to each other. Note that the guard 41 and the probe 9 in a Stage A are engaged by forming a contact between the trigger 44 and flange 42. The guard 41 may encircle the probe 9, but alternatively it may be located just in a close proximity to the probe 9. In most of the medical applications, they should be separated by a distance ranging from 1 to 10 mm.

When the skin 1 moves toward the outer rim 32 of the guard 41 (or vice versa—the guard moves toward the skin) in a direction 47 (FIG. 10-B) and the skin pushes the guard 41 inside housing 40, the following happens. Both the guard 41 and probe 9 move rightward and thus compressing both springs 36 and 46. When the guard 41 moves, the trigger 44 (a part of the guard 41) drugs the probe 9 by the flange 42 (a part of the probe 9) in the same direction. The contacts of the switch 22 are being pressed by the shaft 43 thus making the switch to go a closed state. This signals the outside circuit (not shown) about the guard movement. When the guard 41 moves far enough, that is to the point illustrated in FIG. 10-B (a trigger Stage B), the pusher 45 (a part of the housing 40) engages with the trigger 44. This makes the trigger 44 to bend in the direction illustrated by arrow 70 and decouple from the flange 42. At this moment, the probe 9 is released and the spring 36 pushes it toward the skin 1 which brings the mechanism to the Stage C (a deployed stage of FIG. 10-C). Note that the spring 46 remains compressed by the guard 41. In this stage, the probe 9 moves quickly in direction 48 and the sensor 8 (a part of the probe 9) plunges into the skin 1. A predetermined force of impression of the sensor 8 into the skin 1 is assured by selection of the spring 36. At the moment when the probe 9 starts moving toward the skin 1, the shaft 43 disengages the contacts of the switch 22 making the switch to revert back to an open state. This signals the external circuit of the probe deployment. After the appropriate medical procedure is complete and a physical contact between the probe (or its sensor 8) and the patient body surface (skin 1) is no longer required, the entire assembly is being moved away from the skin 1. The spring 46 pushes the guard 41 outwardly back to its standby position and the mechanism re-cocks to its Stage A as in FIG. 10-A. The device is now ready for repeating another action in the same manner as described above.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

What is claimed is:

1. A temperature measuring medical device, comprising:
a housing;
a probe located at least partially within said housing and configured to be moved relative to said housing between a first position spaced from the skin of a person, and a second position for contact with the skin of the person;
a sensor on a distal end of said probe and configured to sense temperature by contact with the skin;
a biasing element operatively coupled to said probe and biasing said probe toward said second position such that said probe is configured to contact the skin with a predetermined force; and
actuating structure cooperating with said probe to move said probe from one of said first or second positions toward the other of said first or second positions.

2. The medical device of claim 1, further comprising:
an electrical switch for signaling actuation of said probe.

3. A temperature measuring medical device comprising:
a probe configured to be moved between a first position spaced from the skin of a person, and a second position for contact with the skin of the person;
a sensor on a distal end of said probe and configured to sense temperature by contact with the skin;
a biasing element operatively coupled to said probe and biasing said probe toward said second position such that said probe is configured to contact the skin with a predetermined force; and
actuating structure cooperating with said probe to move said probe from one of said first or second positions toward the other of said first or second positions;
wherein said biasing element comprises a buckling column, said buckling column having a first stable configuration and a second stable configuration; and
wherein said actuating structure comprises:
a pivotable lever extending between said buckling column and said probe, said lever having a first configuration corresponding to said first position of said probe and said first stable configuration of said buckling column, and having a second configuration corresponding to said second position of said probe and said second stable configuration of said buckling column, and
a button cooperating with said lever, said button initiating movement of said lever from said first configuration to said second configuration when depressed.

4. The medical device of claim 3, further comprising a second biasing element associated with said button and urging said button in a direction to cause said lever to move toward said first position.

5. The medical device of claim 3, further comprising:
an electrical switch for signaling actuation of said probe;
said lever engaging said electrical switch to activate said switch.

6. The medical device of claim 3, wherein said buckling column comprises a spring.

7. The medical device of claim 1, wherein said actuating structure comprises:
a guard surrounding said probe, said guard movable between a first position wherein said sensor on said probe is positioned within said guard and is spaced from a distal end of said guard, and a second position wherein said sensor is positioned at said distal end of said guard for contact with the skin;
a frame;
said probe coupled to said frame by said biasing element;
a tooth on said guard; and
a finger on said frame;
said tooth engaging said finger when said guard is in said first position and resisting movement of said guard from said first position to said second position until a predetermined force urging said guard toward said second position is applied to said guard.

8. The medical device of claim 7, further comprising:
an electrical switch for signaling actuation of said probe;
wherein said guard in said second position activates said switch.

9. The medical device of claim 1, wherein said actuating structure comprises:
a guard surrounding said probe and movable within said housing between a first position and a second position;
a trigger on said guard, said trigger operatively engaging said probe such that said probe moves with said guard from said first position of said guard to said second position of said guard; and
a pusher on said housing, said pusher engaging said trigger at said second position of said guard to release said probe for movement independent of said guard to said second position of said probe;
said biasing member biasing said probe toward said second position when said pusher engages said trigger to release said guard.

10. The medical device of claim 9, further comprising:
a second biasing member biasing said guard in a direction toward said first position.

11. The medical device of claim 9, further comprising:
an electrical switch for signaling actuation of said probe;

wherein said switch is operatively activated by said probe when said probe is moved with said guard toward said second position of said guard.

12. The medical device of claim 1, wherein said sensor is a contact-type temperature sensor.

13. The medical device of claim 1, wherein said actuating structure moves said probe toward said second position at a predetermined rate of motion.

14. A thermometer, comprising:
a housing;
a probe located at least partially within said housing and configured to be moved relative to said housing between a first position spaced from the skin of a person, and a second position for contact with the skin of the person;
a contact-type temperature sensor on a distal end of said probe and configured to sense temperature by contact with the skin;
a biasing element operatively coupled to said probe and biasing said probe toward said second position such that said probe is configured to contact the skin with a predetermined force;
actuating structure cooperating with said probe to move said probe from one of said first or second positions toward the other of said first or second positions; and
an electrical switch signaling actuation of said probe.

15. The thermometer of claim 14, wherein:
said biasing element comprises a buckling column, said buckling column having a first stable configuration and a second stable configuration; and wherein
said actuating structure comprises:
a pivotable lever extending between said buckling column and said probe,
said lever having a first configuration corresponding to said first position of said probe and said first stable configuration of said buckling column, and having a second configuration corresponding to said second position of said probe and said second stable configuration of said buckling column, and
a button cooperating with said lever, said button initiating movement of said lever from said first configuration to said second configuration when depressed.

16. The thermometer of claim 14, wherein said actuating structure comprises:
a guard surrounding said probe, said guard movable between a first position wherein said contact-type temperature sensor on said probe is positioned within said guard and is spaced from a distal end of said guard, and a second position wherein said contact-type temperature sensor is positioned at said distal end of said guard for contact with the skin;
a frame;
said probe coupled to said frame by said biasing element;
a tooth on said guard; and
a finger on said frame;
said tooth engaging said finger when said guard is in said first position and resisting movement of said guard from said first position to said second position until a predetermined force urging said guard toward said second position is applied to said guard.

17. The thermometer of claim 14, wherein said actuating structure comprises:
a guard surrounding said probe and movable within said housing between a first position and a second position;
a trigger on said guard, said trigger operatively engaging said probe such that said probe moves with said guard from said first position of said guard to said second position of said guard; and
a pusher on said housing, said pusher engaging said trigger at said second position of said guard to release said probe for movement independent of said guard to said second position of said probe;
said biasing member biasing said probe toward said second position when said pusher engages said trigger to release said guard.

18. The thermometer of claim 14, wherein said actuating structure moves said probe toward said second position at a predetermined rate of motion.

19. A temperature measuring medical device, comprising:
a probe configured to be moved between a first position spaced from the skin of a person, and a second position for contact with the skin of the person;
a sensor on a distal end of said probe and configured to sense temperature by contact with the skin;
a biasing element operatively coupled to said probe and biasing said probe toward said second position such that said probe is configured to contact the skin with a predetermined force; and
actuating structure cooperating with said probe to move said probe from one of said first or second positions toward the other of said first or second positions;
wherein said biasing element comprises a buckling column, said buckling column having a first stable configuration and a second stable configuration.

* * * * *